(12) United States Patent
Brinz et al.

(10) Patent No.: US 8,368,747 B2
(45) Date of Patent: Feb. 5, 2013

(54) DEVICE FOR OPTICAL CHARACTERIZATION

(75) Inventors: Thomas Brinz, Bissingen A.D. Teck (DE); Thomas Seiffert, Gerlingen (DE)

(73) Assignee: Robert Bosch GmbH, Stuttgart (DE)

( * ) Notice: Subject to any disclaimer, the term of this patent is extended or adjusted under 35 U.S.C. 154(b) by 616 days.

(21) Appl. No.: 12/448,687

(22) PCT Filed: Dec. 28, 2007

(86) PCT No.: PCT/EP2007/064609
§ 371 (c)(1),
(2), (4) Date: Mar. 31, 2010

(87) PCT Pub. No.: WO2008/092537
PCT Pub. Date: Aug. 7, 2008

(65) Prior Publication Data
US 2010/0201792 A1    Aug. 12, 2010

(30) Foreign Application Priority Data

Jan. 29, 2007   (DE) .......................... 10 2007 004 346

(51) Int. Cl.
*A62B 1/04*    (2006.01)
*A61B 1/04*    (2006.01)
*H04N 7/18*    (2006.01)

(52) U.S. Cl. .............. 348/67; 348/68; 348/69; 348/127; 348/128; 348/131; 348/132; 348/135

(58) Field of Classification Search .............. 348/67–69, 348/127, 128, 131, 132, 135
See application file for complete search history.

(56) References Cited

U.S. PATENT DOCUMENTS

| 4,118,625 | A | | 10/1978 | Underwood |
| 5,428,447 | A | * | 6/1995 | Toida ............................ 356/601 |
| 5,774,214 | A | | 6/1998 | Prettyjohns |
| 5,936,739 | A | * | 8/1999 | Cameron et al. ............. 356/441 |
| 2002/0063215 | A1 | | 5/2002 | Yagita |
| 2005/0105097 | A1 | * | 5/2005 | Fang-Yen et al. ............ 356/497 |
| 2006/0244959 | A1 | | 11/2006 | Yagita |
| 2007/0159690 | A1 | * | 7/2007 | Ulrich et al. .................. 359/385 |
| 2008/0151226 | A1 | * | 6/2008 | Hecker et al. .................. 356/73 |

FOREIGN PATENT DOCUMENTS

| DE | 101 33 104 | 1/2003 |
| EP | 1 241 467 | 9/2002 |
| WO | WO 2006/011803 | 2/2006 |

* cited by examiner

*Primary Examiner* — Tonia L Dollinger
*Assistant Examiner* — Clarence John
(74) *Attorney, Agent, or Firm* — Kenyon & Kenyon LLP

(57) ABSTRACT

A device for optical characterization of a sample is provided, the sample being accommodated in a receptacle container transparent to light. The device includes a camera, using which the sample may be detected, and a first light source is situated in such a way that the sample is transilluminated opposite to the viewing direction of the camera, a second light source is situated on the same side as the camera, and a laser source is situated transversely to the viewing direction of the camera.

11 Claims, 1 Drawing Sheet

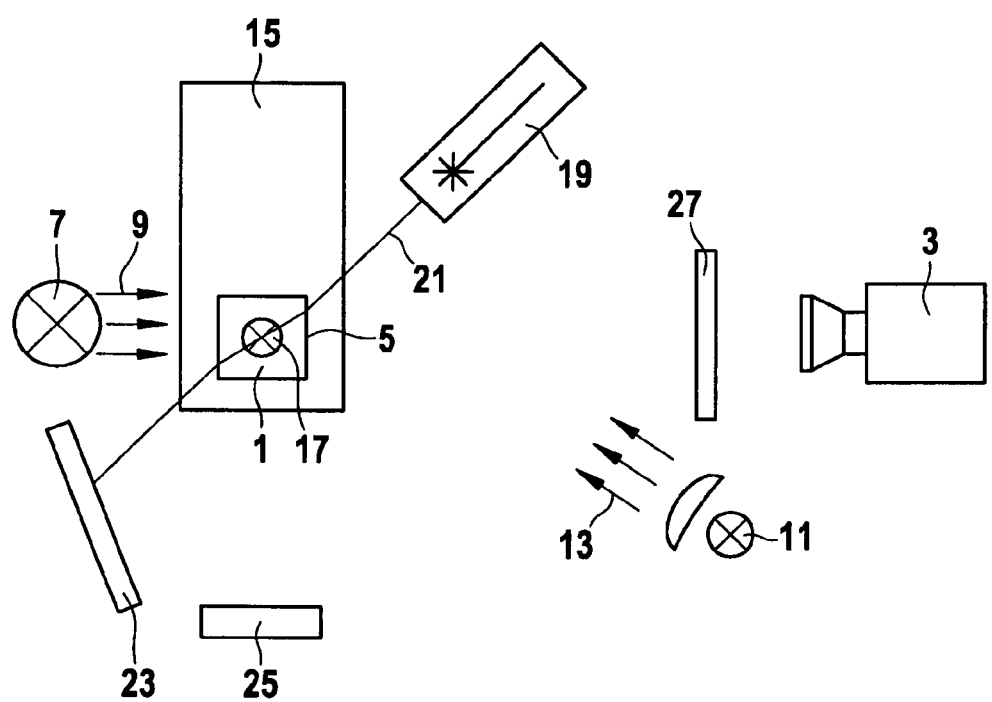

DEVICE FOR OPTICAL CHARACTERIZATION

BACKGROUND OF THE INVENTION

1. Field of the Invention

The present invention relates to a device for optical characterization of samples.

2. Description of Related Art

Samples in the meaning of the present invention are any substances whose properties may be optically ascertained. In particular, samples in the meaning of the present invention are liquids. Properties which are to be studied are, for example, adsorption, reflection, phase formation, and further visible features, such as foaming, etc.

Adsorption and reflection are generally determined by spot-measuring methods. In such a method, the sample is scanned vertically downward using a sensor having two photodiodes. Such a sensor is, for example, the sensor TURBISCAN™ from Quantachrome GmbH & Co. KG.

The spot sensors used for the adsorption and reflection measurement fail in particular, however, if the properties change spatially inside the liquid. This is the case, for example, for the characteristic of foaming or if at least one phase boundary exists in the liquid. Different individual sensors are thus necessary to study the particular property. Sensors for measuring properties which change over the spatial extension of the sample are often also not available.

BRIEF SUMMARY OF THE INVENTION

In a device implemented according to the present invention for the optical characterization of samples, the sample being accommodated in a receptacle container transparent to light, and a camera being provided, using which the sample may be detected, a first light source is situated in such a way that the sample is transilluminated opposite to the viewing direction of the camera. A second light source is situated on the same side as the camera and a laser source is situated transversely to the viewing direction of the camera.

Transversely to the viewing direction of the camera means that the laser is not situated in or opposite to the viewing direction of the camera, but rather at an arbitrary angle thereto. If a cuvette is used as the sample container, in which the sides are opaque to the laser light, the laser is preferably not situated at an angle of 90° to the viewing direction of the camera. If a sample container having transparent side walls is used, a configuration in which the laser assumes an angle of 90° to the camera is also possible.

Using the device according to the present invention, the determination of a plurality of properties using a single measurement is possible due to the different light sources which transilluminate the sample from different sides. The analysis of the images recorded by the camera is typically performed by an electronic analysis system. This is a computer, for example.

For example, in the case of an opaque sample, the index of refraction may be determined using the laser beam generated by the laser source by the penetration of the laser light on the sample itself.

The laser source is preferably a wide-line laser. It transilluminates the sample, so that the penetration, the so-called Tyndale effect, may be measured.

A screen is preferably provided, which is positioned in such a way that a projection of the laser beam which has penetrated the sample may be detected by the camera on the screen. A projection of the laser line of the widened wide-line laser results on the screen. If particles are dispersed in the sample, the particle size may be determined on the basis of the diffraction of the laser light by projecting the laser line.

All laser sources known to those skilled in the art whose lasers may be widened to a line are suitable as the laser source. A restriction of the wavelength is not provided, but the detector—the camera in the scope of the present invention—must be able to detect this wavelength. Suitable laser sources are, for example, a red helium-neon laser having a wavelength of 632 nm or a green laser having a wavelength of 523 nm.

In a further example embodiment, a mirror is situated below the sample, which allows a view of the bottom of the sample. For this purpose, the mirror is inclined in such a way that an image of the bottom of the sample falling on the mirror is reflected in the direction of the camera. For example, the settling of suspended materials in the sample may be observed with the aid of the mirror. To be able to observe the settling of the suspended materials, a transparent lighting system for transilluminating the entire sample is necessary. A further light source is preferably situated above the sample for this purpose.

If the sample contains dispersed particles therein, the strength of the light penetration and the penetration depth of the laser in the lower part of the sample may be determined directly due to the laser source being situated transversely to the viewing direction of the camera. The strength of the diffraction of the particles may be measured directly by the width of the line imaging of the linear laser. In addition, the backscatter of the laser may also be observed for the entire sample.

In a further example embodiment, at least one further laser source is provided, which is situated transversely to the viewing direction of the camera. The laser sources are preferably situated in such a way that the laser beams emitted by the laser sources penetrate the sample in such a way that the projections of the laser beams adjacent to one another on the screen may be detected by the camera. Multiple independent measurements are obtained by the use of multiple laser sources. This has the result that the particle size of particles dispersed in the liquid may be evaluated better.

The multiple lasers may generate laser beams having identical or different wavelengths. For identical wavelengths, measurements are preferably made spatially offset at different points in the sample. For different wavelengths, measurements may also be made at the same point of the sample. The advantage of the use of laser sources which generate laser beams having different wavelengths is that a separation of the information in the camera is made easier.

In a further example embodiment, a UV source, for irradiating the sample, and a detector are provided to determine the luminescence and/or the fluorescence of the sample. Because the camera is generally not sensitive to UV light, this illumination does not interfere with the camera. However, if the detecting spectrum of the camera and the measuring spectrum of the fluorescence or the luminescence overlap, it is necessary to keep in mind the direction in which the sample is illuminated. It is preferable for this purpose for the UV source to illuminate the sample from the side—seen from the viewing direction of the camera.

In a further example embodiment, a device for recording infrared radiation is situated in such a way that infrared radiation originating from the sample is recorded. The heat distribution in the sample may be measured by recording the infrared radiation. Thus, for example, the reaction progress may be tracked in reactions or the mixing progress may be tracked in mixtures. The device for recording the infrared radiation is an infrared-sensitive camera, for example. If an infrared-sensitive camera is used, for example, the difference in the heat capacity or the heat conductivity may also be measured using active thermography. For this purpose, first an image of the sample is recorded using the infrared-sensitive camera. After the image has been recorded, an infrared flash is emitted and an image is again recorded using the infrared-sensitive camera. A difference in the heat absorption by the sample may be recognized by comparing the two images which have been recorded using the infrared-sensitive camera. If further images are subsequently recorded using the infrared-sensitive camera, it may also be seen how rapidly the heat delivered by the infrared flash penetrates into the sample, i.e., the sample cools down again. A further advantage of active thermography is also that a mixing procedure may be observed and evaluated therewith.

To detect whether small quantities of sediment or particles are contained in the sample, it is preferable for the sample to be accommodated rotatably, to be able to swirl up the particles. In addition, multiple independent recordings are possible due to the rotation of the sample, whereby the quality of the measurement may be increased.

In a further example embodiment, at least one tunable filter is provided, to allow a decomposition of the recording into individual spectra. The at least one tunable filter element is preferably situated between the sample and the camera. By placing the filter element between the sample and the camera it is sufficient to only provide one single filter element. A separate filter element does not have to be provided on each light source. The recording may be decomposed into narrow-band spectra by using the at least one tunable filter element. A higher spectral separation is achieved by decomposition into spectra than when using a standard RGB color camera. In this way, phase boundaries may also be registered better, if the different substances only have a slight color difference.

Finally, the contact angle between the sample and the receptacle container may also be determined using the device according to the present invention. The contact angle results on the one hand from the surface tension of the at least one liquid in the receptacle container and the adhesion between the sample and the material of the receptacle container. The receptacle container is preferably a cuvette.

BRIEF DESCRIPTION OF THE DRAWING

The single FIGURE shows a schematic illustration of a device implemented according to the present invention for the characterization of samples.

DETAILED DESCRIPTION OF THE INVENTION

A schematic top view of a device implemented according to the present invention for the optical characterization of samples is shown in the single FIGURE.

A sample 1 is recorded by a camera 3 for the optical characterization. Sample 1 is generally a liquid which is accommodated in a receptacle container 5. Receptacle container 5 may be a cuvette, for example. To be able to optically characterize sample 1, it is necessary for receptacle container 5 to be transparent to radiation in the required wavelengths. The receptacle container may be manufactured from an amorphous plastic, such as PMMA, or also from glass or quartz glass, for example.

A first light source 7 is situated in such a way that sample 1 is transilluminated opposite to the viewing direction of camera 3. The emitted light of first light source 7 is shown by arrows 9. Sample 1 is transilluminated by first light source 7. For example, the spatial distribution inside the sample may be determined in the transmitted light upon adsorption. Thus, for example, the phase boundaries may be recognized. Further recognizable features in the view resulting using transmitted light are foam or the more or less pronounced character of the meniscus, for example. Large particles having an optically differing refractive index may also be recognized. For example, the surface tension of the liquid in receptacle container 5 may be determined from the meniscus.

A second light source 11 is situated on the same side as camera 3. Second light source 11 may either be situated adjacent to camera 3 or also enclose the camera objective as a ring light. If a ring light or a coaxial incident light is used, the quality of the reflection measurement is improved.

The spectral reflection in the visible range may be spatially measured with the aid of the light emitted by second light source 11, which is shown here by arrows 13. In addition, viewing the bottom of sample 1 is also made possible. A mirror 15 is situated below sample 1 for this purpose. Mirror 15 is oriented in such a way that the bottom of sample 1 may be registered using camera 3. For example, the sedimentation of particles contained in sample 1 may be recognized on the bottom of the sample. Furthermore, it may be recognized with the aid of the illumination by second light source 13 whether foam has formed on sample 1, how pronounced the meniscus is, and whether a deposit has formed in receptacle container 5. Furthermore, phase boundaries are also recognizable by adsorption differences, for example.

To recognize the sedimentation behavior, it is alternatively also possible to provide a further light source 17 instead of second light source 13, which is positioned above sample 1. The sample is transilluminated from above using further light source 17.

A laser source 19 is situated transversely to the viewing direction of the camera. A laser beam 21, which transilluminates sample 1, originates from laser source 19. Laser source 19 is oriented in such a way that laser beam 21 does not run at a right angle to the viewing direction of camera 3. This is necessary in particular if the sides of receptacle container 5 are not transparent to the laser light. In this case, it is necessary for laser beam 21 to be guided from front to back through sample 1, but not to lie in the viewing direction of camera 3. If receptacle container 5 is also transparent to the laser light on the sides, it is thus also possible to guide laser beam 21 through the side. In this case, a configuration in which laser beam 21 is situated at a right angle to the viewing direction of camera 3 may also be used. A screen 23 is situated behind sample 1 viewed from laser source 19, using which laser beam 21 is reflected, so that it may be seen by camera 3. Laser beam 21 which is generated by laser source 19 is preferably a widened wide-line laser. For example, the penetration of sample 1 may be measured using the laser. The so-called Tyndale effect is generated by the scattered light of small particles which are contained in the sample. This effect allows the Mie scattering of sample 1 to be determined. If submicroscopic particles are contained in sample 1, the scattering of the laser light is also visible in the sample itself.

A laser line may be seen on screen 23. The index of refraction of sample 1 may be determined by the location of the laser line on screen 23. The intensity of the laser line on screen 23 indicates the attenuation by adsorption by particles in sample 1. The more light is diffracted on particles in sample 1, the more the laser line is widened. In this way, the mean particle diameter of the particles contained in sample 1 and the mean particle count may be determined.

If sample 1 strongly adsorbs the penetrating light, this strength may be determined to be spatially distributed directly into the sample upon penetration of laser beam 21.

The penetration may be read off directly on the bottom of the sample. It is reflected from mirror 15 and deflected onto camera 3.

To be able to better determine the size of particles contained in the sample, it is possible to provide at least one further laser source in addition to laser source 19 shown in the FIGURE. If the individual laser beams emitted by laser sources 19 penetrate the sample in different positions, a larger area of the sample is studied simultaneously. Laser beams 21 emitted by individual laser sources 19 may have identical wavelengths or also different wavelengths. If laser beams 21 having different wavelengths are used, it is possible that the laser beams each penetrate sample 1 at the same position. Because of the different wavelengths, better results are also achieved upon penetration of sample 1 at the same position. If different wavelengths are used, the information of individual laser beams 21 which is registered by the camera may be separated and analyzed individually. For example, it is possible to use a filter to separate the different wavelengths.

In addition to light sources 7, 11, 17 shown in the FIGURE, it is also possible to irradiate the sample using UV light. For this purpose, a UV source 25 is additionally provided. For example, fluorescence or luminescence measurements may be integrated with the aid of the UV light. Because camera 3 is typically not UV-sensitive, this illumination does not interfere with the remaining measurements. In addition to UV source 25, a UV detector, using which the fluorescence or luminescence of the sample may be determined, is also necessary. Like camera 3, the UV detector is preferably also connected to an electronic analysis unit, in which the ascertained data may be detected directly and possibly processed further. As shown in the FIGURE, UV source 25 is preferably situated transversely to the viewing direction of camera 3. For example, the UV detector may be implemented with UV source 25 as one component. Alternatively, it is also possible that UV source 25 and the UV detector are two different parts. It is not necessary for UV source 25 and UV detector to be situated on the same side of the sample. Transmission or reflection may be determined as a function of the configuration of the UV detector. With a concurrent configuration on both sides, transmission and also reflection may be determined.

To be able to measure the heat distribution in sample 1, it is possible to provide a further camera, which is infrared-sensitive, in addition to camera 3. It is also possible to use a camera which may make recordings both in the visual range and also in the infrared range. For example, the progress of a reaction which is conducted or the progress of mixing may be tracked with the aid of the heat distribution in sample 1. The difference in thermal capacities or heat conductivity may also be measured using an infrared-sensitive camera with the aid of active thermography, for example. For this purpose, however, it is necessary to also provide an infrared source in addition to the infrared-sensitive camera. The infrared source may be situated at any arbitrary position with respect to the sample. However, the infrared source is preferably situated on the same side as the infrared-sensitive camera, because the penetration behavior of the thermal radiation is determined by active thermography. The reaction of the sample is more rapidly visible if the infrared source is situated on the same side as the camera.

To measure differences in the heat capacity or the heat conductivity with the aid of active thermography, first a recording of sample 1 is made using the infrared-sensitive camera. An infrared light flash is subsequently emitted by the infrared source. This has the result that sample 1 heats up. After the infrared light flash is emitted, a further recording of sample 1 is made. This shows the local heating of the sample by the infrared light flash. The way in which sample 1 cools back down may be tracked by subsequent further recordings of the sample with the aid of the infrared-sensitive camera. In the event of a uniform distribution of heat conductivity or heat capacity of the sample, the cooling occurs uniformly. If the sample has local differences in heat conductivity or heat capacity, the cooling will also occur at different rates. Parts of the sample remain warm longer than other parts.

Sample 1 is preferably movably accommodated. In this way, particles contained in sample 1 may be swirled up, for example. It may thus be recognized whether particles are contained in sample 1 at all, and it may be tracked how rapidly sedimentation of the particles occurs. The quality of the determination is thus improved.

To allow a decomposition of the recording into individual spectra, it is further possible to use a filter 27. Filter 27 is preferably a tunable filter which permits different wavelengths of the light to pass through as a function of the setting. For a single filter 27 to be sufficient, it is preferably placed directly in front of camera 3, as shown in the FIGURE.

What is claimed is:

1. A device for optical characterization of a sample accommodated in a receptacle container transparent to light, the sample being detected by a camera, the device comprising: a first light source situated in such a manner that the sample is trans-illuminated opposite to the viewing direction of the camera; a second light source situated on the same side as the camera; at least one laser source situated transversely to the viewing direction of the camera;
    a screen positioned in such a manner that a projection of a laser beam from the laser source, which laser beam has penetrated the sample, is detected on the screen by the camera; and
    at least one further laser source situated transversely to the viewing direction of the camera.

2. The device as recited in claim 1 further comprising: a mirror situated below the sample, wherein the mirror enables viewing of the bottom of the sample.

3. The device as recited in claim 1, wherein laser beams emitted by the laser sources penetrate the sample in such a way that projections of the laser beams are detected adjacent to one another on the screen by the camera.

4. The device as recited in claim 3, wherein the laser sources generate laser beams having different wavelengths.

5. The device as recited in claim 3, further comprising:
    a UV source for irradiating the sample; and
    a detector configured to determine at least one of luminescence and fluorescence of the sample.

6. The device as recited in claim 3, further comprising:
    a device for recording infrared radiation, wherein the device for recording infrared radiation is situated in such a manner that infrared radiation originating from the sample is recorded.

7. The device as recited in claim 6, wherein the device for recording infrared radiation is an infrared-sensitive camera.

8. The device as recited in claim 7, further comprising:
    a device for emitting an infrared flash onto the sample.

9. The device as recited in claim 6, further comprising:
    at least one tunable filter element, wherein the filter element enables separation of the recording into individual spectra.

10. The device as recited in claim 9, wherein the at least one tunable filter element is situated between the sample and the camera.

11. The device as recited in claim 9, wherein the sample is rotatably accommodated in the receptacle container.

* * * * *

UNITED STATES PATENT AND TRADEMARK OFFICE
CERTIFICATE OF CORRECTION

PATENT NO. : 8,368,747 B2
APPLICATION NO. : 12/448687
DATED : February 5, 2013
INVENTOR(S) : Brinz et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 861 days.

Signed and Sealed this
First Day of September, 2015

Michelle K. Lee
*Director of the United States Patent and Trademark Office*